United States Patent [19]
Smallbone

[11] Patent Number: 5,627,874
[45] Date of Patent: May 6, 1997

[54] X-RAY SPECTROSCOPIC ANALYSIS OF POWDER SAMPLES USING A WINDOW-LESS CELL SYSTEM

[76] Inventor: Allan H. Smallbone, 2905 Piedmont Ave., La Crescenta, Calif. 91214-3840

[21] Appl. No.: 417,001
[22] Filed: Apr. 5, 1995
[51] Int. Cl.$^6$ .................................. G01N 23/223
[52] U.S. Cl. .................................. 378/208; 378/44
[58] Field of Search .................. 378/45, 47, 208, 378/44

[56] References Cited

U.S. PATENT DOCUMENTS

4,643,033  2/1987  Solazzi .......................... 378/208
5,323,441  6/1994  Torrisi et al. ..................... 378/208

*Primary Examiner*—Don Wong

[57] ABSTRACT

An improved method of assaying powdered samples of minerals, ores, concentrates, raw mix cement, phosphates and other processed minerals in either an On-line or in-process X-ray fluorescence laboratory analytical system, using a Window-less cell system. The cell system is constructed with four walls, a closed and open side. The open side is the uppermost side facing an inlet chute as it travels into the chute to permit the filling and discharge of samples.

3 Claims, 8 Drawing Sheets

X-RAY SPECTROSCOPIC ANALYSIS OF POWDER SAMPLES USING A WINDOWLESS CELL SYSTEM

CROSS REFERENCE TO RELATED APPLICATIONS

Smallbone, in U.S. Pat. No. 3,388,427 dated 1968, designed an automatic briquette making machine to duplicate laboratory methods of preparing raw mix cement and similar dry materials for X-ray analysis.

Carr-Brion et al, in U.S. Pat. No. 3,443,092 dated 1969, designed a system to analyze the solid component of a slurry.

Smallbone and Gurvich in U.S. Pat. No. 4,134,012, in 1979 employed a primary X-ray beam having two widely different wavelength areas of analysis and were able to obtain on-line analytical data of lighter elements such as calcium in a heavy metallic ore slurry and also data relating to slurry density and particle size, thus enabling greater accuracy to be obtained for all elements of interest.

Robertson in U.S. Pat. No. 5,020,084 in 1991 teaches an ore analysis device using X-ray-ray fluorescence to measure samples of gold having 10 ppm by mass.

Sipila et al in U.S. Pat. No. 5,107,527 in 1992 teaches a device for analyzing sludgy materials by exposing the flowing material in continuous action to X-ray radiation.

Smallbone in U.S. Pat. No. 5,272,745 dated December 1993 designed a system for analyzing continuously flowing dry powder samples by means of X-Ray fluorescence spectroscopy.

SUMMARY OF THE INVENTION

To extract the desired minerals efficiently from an ore, or to effectively produce an optimum product from a mixture of minerals, a rapid on-line or in-product assay of the elements composing the mixture of minerals involved, is essential. Standard laboratory assays, while accurate, are expensive, time consuming and are rarely related to production in real time. The small quantity of sample normally extracted for such assays, from the immense volumes usually encountered in such production, is generally not well related to the information needed for accurate control. For example, assaying one ounce of the product an hour, with the results being only available to the process personnel the following day, may not be at all indicative of the exact nature of the 30,000 tons that passed through the concentrator in that same day. In addition the ratio of sample to product flow is greater than 1 in 4,000,000, which is excessive and the time delay of many hours effectively makes control extremely difficult.

With such a need for timely and relatively accurate assays being critical to the vast majority of processes, on-stream elemental analysis of products is now accepted as a necessity in slurried and liquid based products.

Current on-line slurry analytical systems using X-ray fluorescence have proved most effective in providing rapid information about the product at a relatively low cost thereby producing an economically efficient product.

However, efforts to assay flowing powders using similar techniques have not yet met the needs of most powder processing industries.

Attempts to improve the accuracy of on-line methods of analysis and minimize errors such as density variations and inter-element effects have been undertaken by using either variations in the secondary X-ray beams or energy emitted from various wavelengths of background and then manipulating these data, or by using various mechanical means to enable samples of a process to be rapidly presented to the X-ray beam for analysis.

In the case of dry powders, progress in automated on-line assay has not evolved as fast as it has in slurry applications. Generally, powders are much more difficult to maintain in a suitable position or perimeter, and once in position are not always amenable to reverting to free flow when required. Powders are reluctant to flow due to changes in humidity, increased surface tension, etc. and leftover particles from previous samples can, in some instances, create inter-sample contamination problems.

In most X-ray laboratory procedures for sample analysis, powder samples are finely ground in a manually controlled off-line grinding mill, to approximately 350 mesh, then mixed and diluted with a binding agent such as boric acid or pure cellulose powder to ensure partial bonding and by using a high pressure press and dies, convert the sample into a hard, cohesive briquette to prevent its subsequent disintegration during handling and analysis.

Great care must be exercised in always grinding sample to precisely the same size of particle and to apply a consistent even pressure in manufacturing the briquette to avoid serious errors in elemental analysis. Adding binder to a sample not only creates a considerable variation in the "sample to bulk" ratio and therefore to the resulting assay when incorrectly related to the bulk process, but even minor errors in additions of binders results in a loss of critical minor elemental intensity. Variations in sample briquetting pressure also introduces similar errors.

Other automated, but unpatented, attempts to copy laboratory powder sample handling standards by either automatically briquetting the powders or fusing dry samples at high temperature have been described in various publications, but they have experienced only small successes in the areas of on-line analysis and control.

There are two major problems when manually sampling either slurry or powder on-line products. Firstly, is the collected sample truly representative of the main product at that time? For example, occasional samples are frequently incorrectly extracted from the main product and while correct in quantity they may not be at all representative of the main product in elemental content, particle size or density mainly due to preferential segregation.

Secondly, the other major error is caused by the inevitable variation of incorrect or accidental dilution of the sample, either by liquid or dry binder additions. In most cases, where the individual samples are correctly diluted, the liquid samples normally contain 30% to 90% water. For powders, the correct amount of added binder is generally 50% boric acid or inert cellulose for soft coals to 75% boric acid for high silicate samples such as sand. This loss in intensity of low Z elements in the sample due to correct dilution, or other unknown variations of critical low concentrations of elemental data but even more so to unknown dilution variations in the dilution factor creates major errors in the dam. These unknown variations can be most critical in obtaining accurate data relating to inter-element corrections and the percentage content of important elements that cause serious upsets in the production of certain minerals. By avoiding all dilution of the sample, whether correct or incorrect, and also eliminating the window through which both primary and secondary X-rays must pass and in so doing deteriorate in intensity, the data increase as well as the validity of the data, can be greatly improved. In addition, the window-less cell has a total available sample area presented for analysis which can be as much 14 times or more than the normal analytical sample area available when compared to a standard sample briquette as assayed in an X -ray analyzer for the same period of time.

This invention takes advantage of the natural state of a main product by continuously analyzing portions of a flow of powder in the 100% normal stage thus obtaining an important increase in the intensity of the secondary X-rays carrying elemental data to the X-ray detectors.

In addition, by completely eliminating the window, these data now contain the all-important minor and major elemental data necessary for inter-element corrections as well as data relating to sample specific gravity, particle size, moisture content and sample cell density. For example, an increase of 50% to 100% in the lower elemental data intensities can result in a large dramatic improvement in data corrections.

These samples, retained within an analyzing cell, are analyzed in turn by one or more individual and different X-ray spectroscopic sources operating at specific and separate wavelengths, and having independent and distinct X-ray detector systems. Analytical data are obtained by measuring essentially the same area and depth of sample at these distinctly different wavelengths of X-ray spectroscopy without the severe loss of intensity due to dilution factors, plastic and metallic windows and other sources of error.

Essentially, samples are collected, retained and transported, within a window-less cell, between one or more different systems of analysis, assayed for all data and then discharged. It is also appreciated that this movement, while currently preferred to be linear, it could readily be of a rotating motion. Analyzing samples continuously in a window-less cell in an on-line processional mode by one or more different X-ray analyzers readily produces large quantities of elemental data which is more meaningful to the main product or production method.

DETAILED DESCRIPTION OF THE INVENTION

In most processing plants, concentrators, beneficiators, mines etc. an assay of incoming material is essential for optimum operation. This initial assay is equally as critical as an assay of the outgoing product of final metallic concentrates or coal blended for low sulfur. A reliable timely primary assay can greatly reduce operating costs, total time needed for production, increased tonnage throughput, decreased power requirements, a decrease in the use of reagents or essential component materials required in the process.

Normal operational use of X-ray fluorescence spectroscopy in operating either X-ray tubes or Radioisotopic materials as sources of energy for X-ray fluorescence spectrometry are well known over decades of use and the employment of different types and models of X-ray detectors are also equally well known to those versed in the profession. Therefore none of these common variables, although they will be used in this invention, will be discussed within this specification.

This invention provides both the desired superior elemental data outputs and an improved powder sample handling apparatus. This invention lies both in the method of collecting, presenting, retaining, transporting, analyzing and discharging samples and also increasing the reliability and accuracy of the analytical data by removing the window that normally lies between the planes of the X-ray tube and the sample and which partially suppresses the transmission of primary X-rays and secondary X-ray radiation transmission. A more rapid assay of the main product covering a greater surface area is also provided, thereby allowing a higher percentage of elemental, particle size, density and moisture data to be gathered and presented to a control system for a more realistic and rapid control of processes at lower cost.

Samples are preferably provided to the sample chute unit, in a fine ground state, of approximately 150 mesh to 350 mesh size. Coarser material may suffer a proportional measured loss in accuracy.

Figure 4:
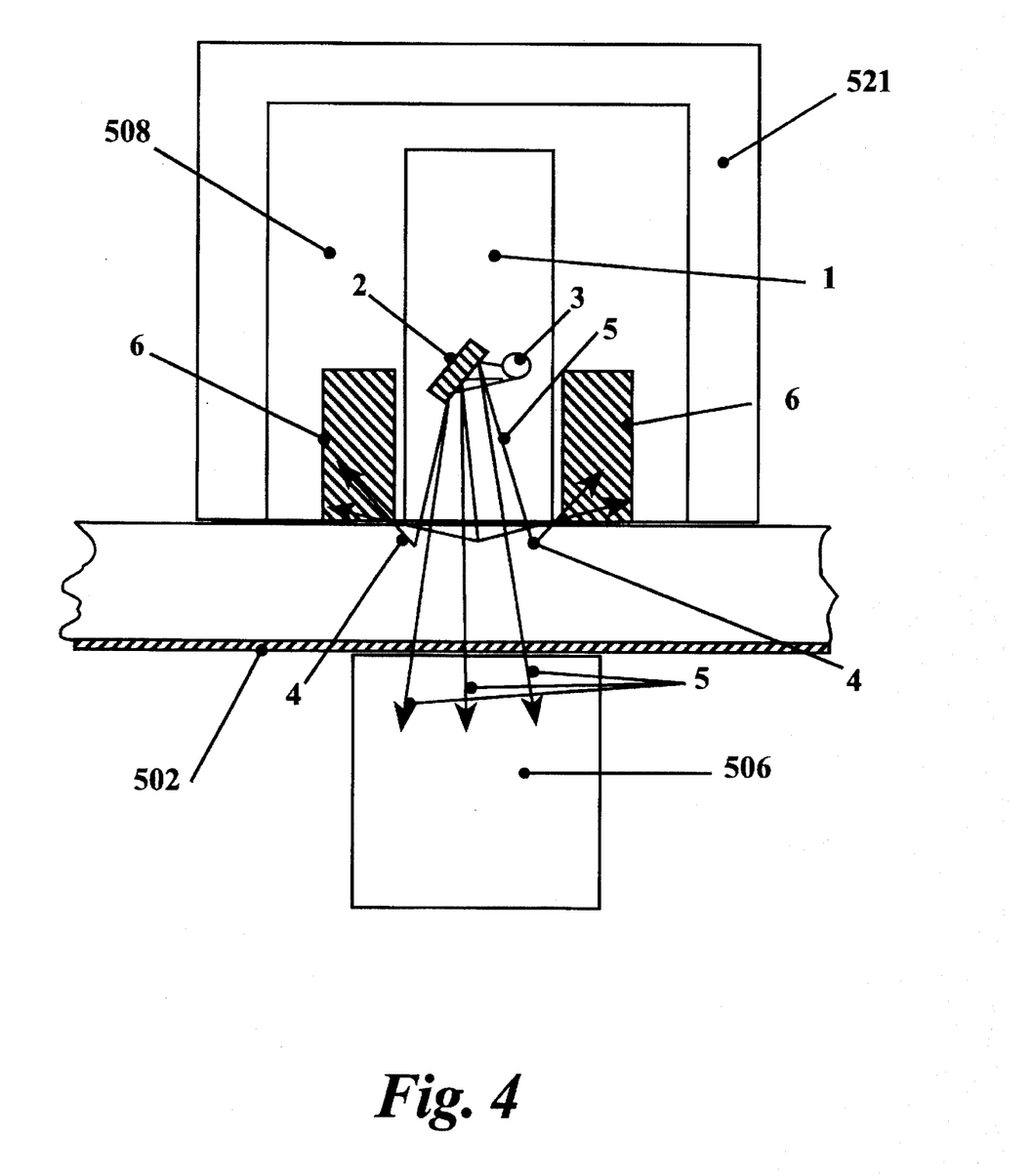
FIG. 4 is an enlarged view of the X-ray spectroscopic systems within 508 and 507 and it depicts a typical X-ray spectroscope as commonly used for the analysis of powders, briquettes, slurries and solids. Also shown for reference purposes to demonstrate the relationship of the X-ray analyzer to the analyzing cell is the Window-less cell 502, 506 is the density detector situated below the cell and the X-ray spectroscope is mounted in 508 and enclosed in 521.
Figure 5:
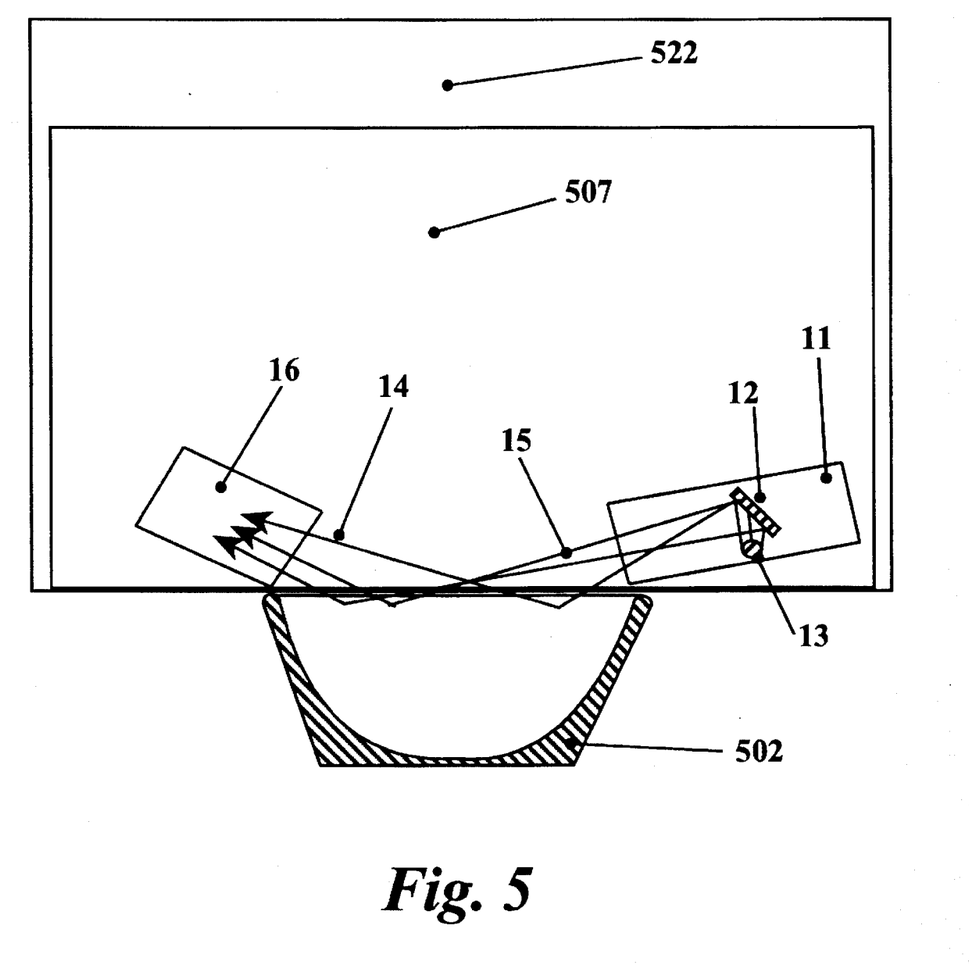
FIG. 5 another enlarged view of a second X-ray spectroscope within 507 and depicts an alternate method of an X-ray spectroscope and the relationship of the X-ray spectroscope to the Window-less cell 502. This X-ray spectroscope may be mounted in 507 and enclosed in 522.
Figure 6:
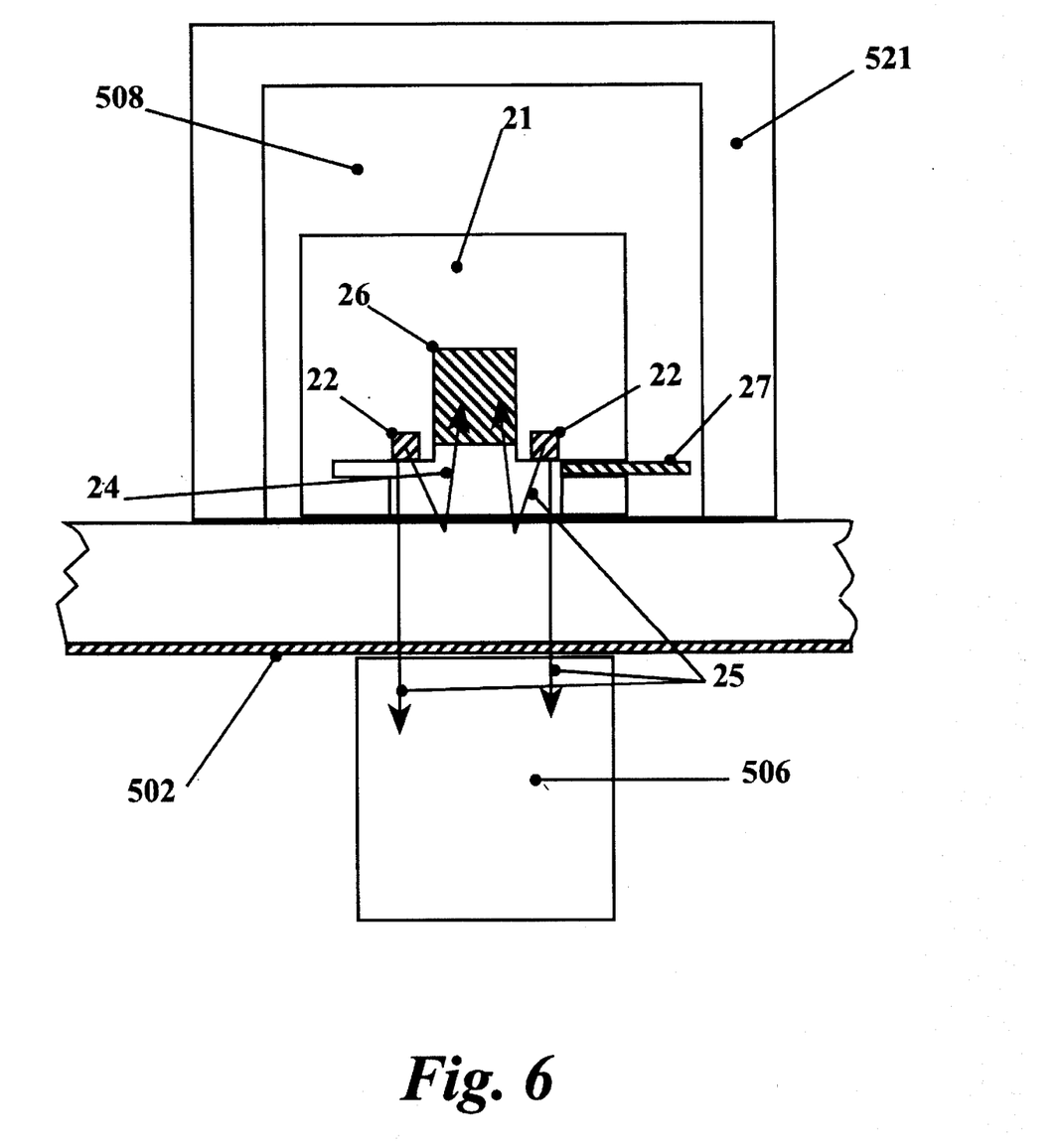
FIG. 6 is also an enlarged view of an X-ray spectroscope and it depicts a third X-ray spectroscope using Radio-active isotopes for the analysis. The relationship of this X-ray system to the Window-less cell is also shown. The cell is 502 and the density detector is 506 and the X-ray system may be mounted in 508 and both enclosed in 521.
Figure 7:
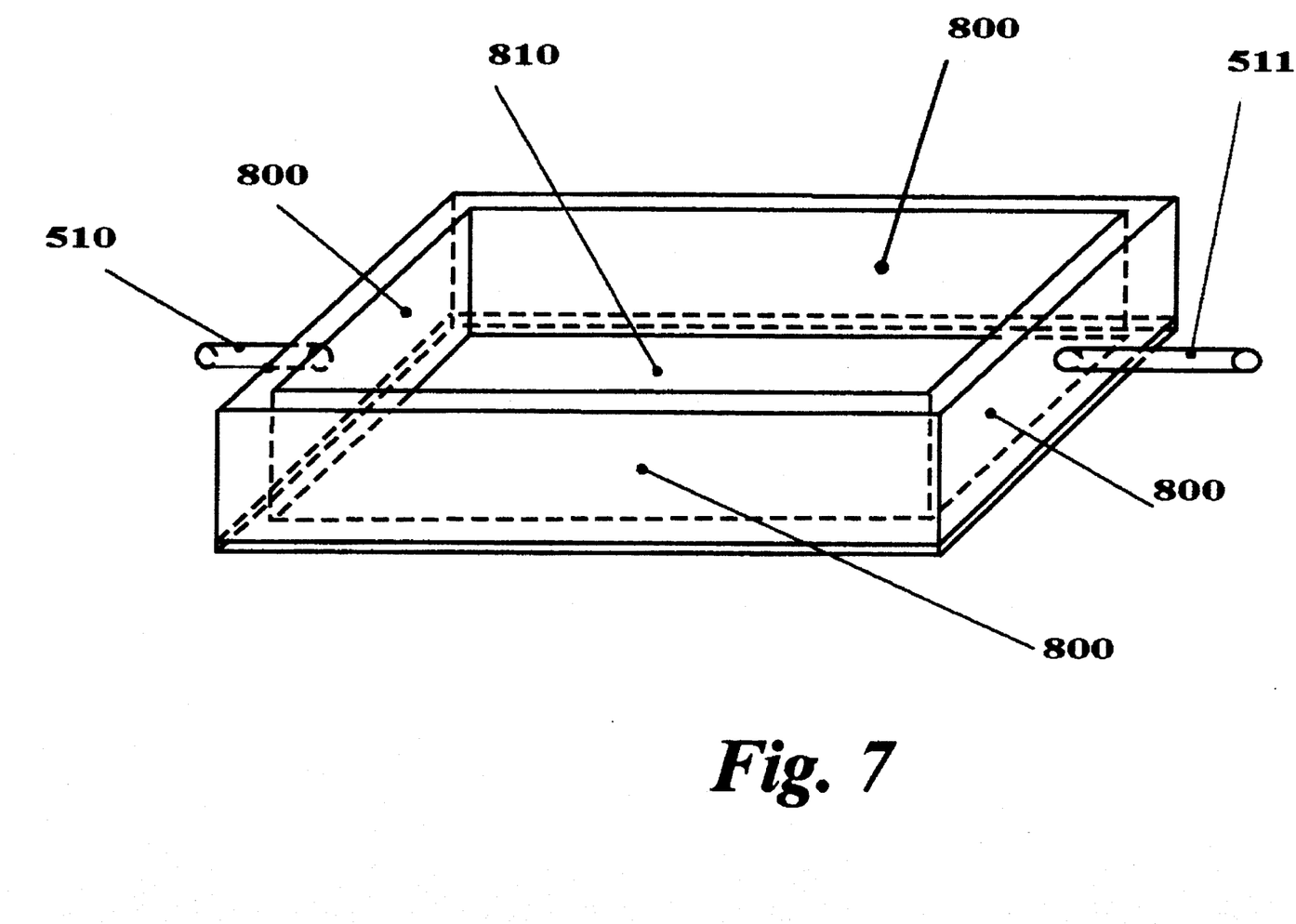
FIG. 7 is an enlarged view of cell (502).

This invention, as previously described in the Summary of the Invention and the accompanying 8 Drawings, FIGS. 1, 1A, 2 and 3, 4, 5 & 6 may use X-ray tubes & X-ray detector systems having different operating characteristics and different excitation targets and in addition different Radio-active Isotope sources having various energy levels and characteristics and optimal detector systems, either separately or collectively mounted within the system. Particular targets for X-ray excitation and the associated detectors, and any radioactive isotope excitation unit together with its associated detector, will be selected dependent on the preferred analytical wavelength, elemental composition of the samples and type of material to be assayed. Three different X-ray analyzing systems are shown in FIGS. 4, 5 & 6. The operating positions for theses X-ray analyzers are shown on the drawings as 507, 508, 521 & 522, and are included only for the purposes of defining how the analysis is conducted. Typical X-ray units as shown are freely available and their operation is well known and are not considered part of the invention. Helium gas atmosphere may also be employed when assaying certain elements or materials.

In the preferred mode of practicing this invention, a portion of a main product stream is continuously sampled to become an automated assay sample stream. The amount of sample extracted is directly related to the product and the desired speed of assays required for product control. For example, for some products, a minimum of 3 cubic inches, up to 30 cubic inches, approximately 2 to 3 lb. of sample, is required every 60 seconds. However, the amount of sample extracted is not critical, either in quantity or frequency. Larger or smaller applications may require more or less sample and the size and volumetric capacity of the cell may be varied to suit. The only requirement is that the sample in the cell be filled to the top and of sufficient quantity to be fully visible to the X-ray analyzer.

Figure 1:
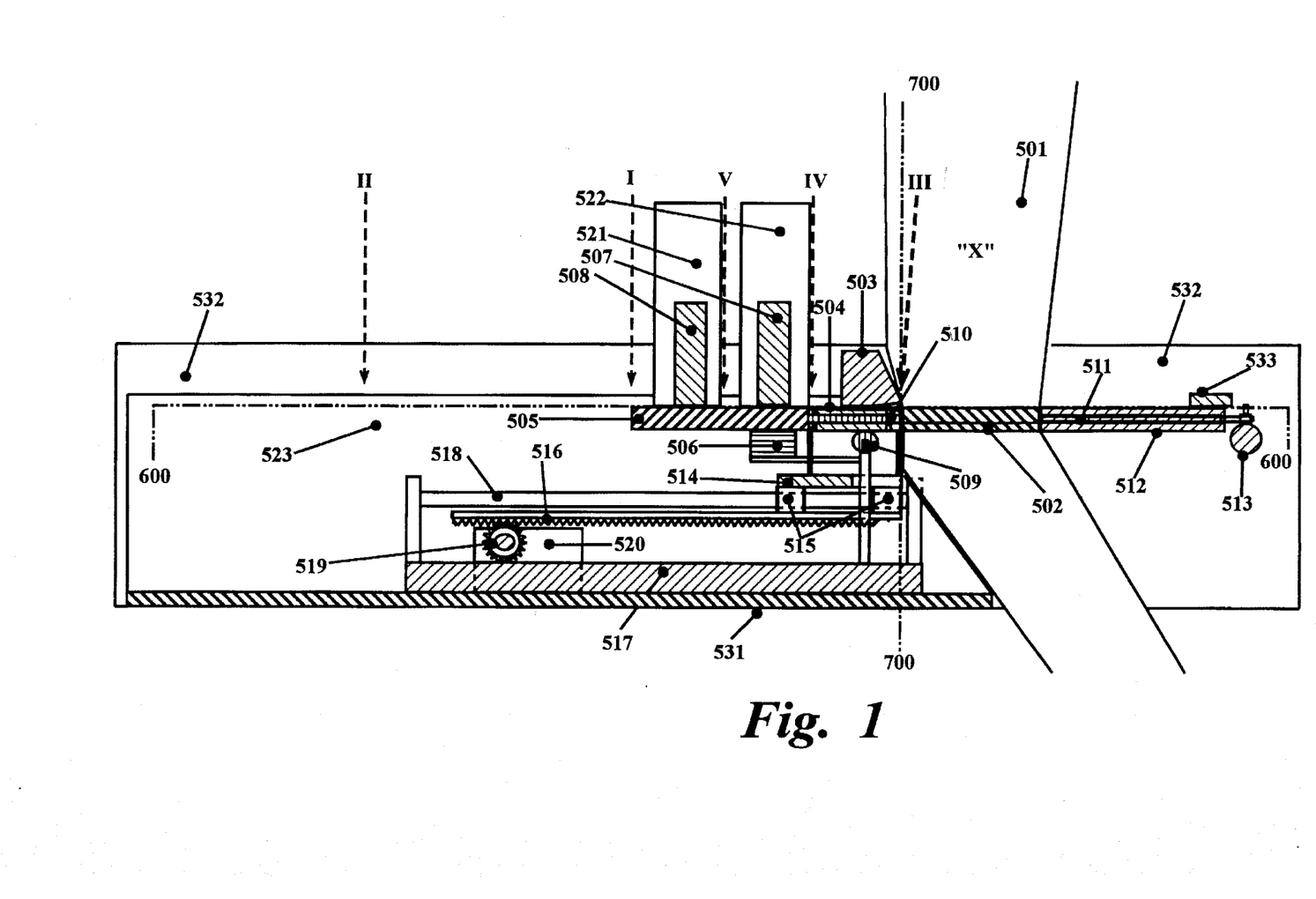
FIG. 1, shows a linear application of the method of selecting, retaining, transporting, analyzing a sample and discharging the sample. This drawing shows the relationship of a sample inlet chute, window-less sample cell transportation unit, window-less sample cell and X-ray spectroscopy units on a side elevation, at section 500—500 of FIGS. 2 & 3. The window-less sample cell 502 is in ate sample loading position, III and the window-less sample cell transportation unit is at position I, ready to start moving toward the left of the drawing.

In FIG. 1, A flowing stream of sample from the main product enters the sample inlet chute 501 at the top "X". The average amount, dependent on window-less sample cell dimensions, ~10–30 cubic inches or more, will over fill the window-less sample cell 502. Excess sample will fall past the window-less cell and continue to the product destination.

The analyzer window-less cell unit is constructed of size suitable for the application and is constructed as in FIGS. 1, 1A, 2, 3 and 7. The window-less sample cell 502 containing the sample is mounted on the sample transporter 514 and is supported over its length by supports 526,527, FIGS. 2 & 3. The cell is constructed with four walls (800), a closed side (810) and an open side. The open side is the uppermost side to permit the acceptance and discharge of powder samples.

The window-less sample cell unit 502,505,504,511 is mounted on the transport carriage 514 which is in mm supported on four linear ball bearings 515 sliding on linear bearing ways 516. All firmly mounted on base support 517.

Power to move the window-less sample cell transport carriage from position III to the analysis positions IV and V and to return the transport carriage to the start position III is provided by the motor drive means 520 and gear 519 through gear shaft 534. FIGS. 1, 1A, 2 & 3.

An initiation signal will start moving the overfilled sample cell 502 and the mechanically linked shutter unit 505, and the X-ray standardizing sample unit 504 and the cell rotation section 511 from the filling position toward the position IV.

As the full window-less sample cell passes through position III, the excess sample in the window-less cell 502 will be removed by the sample compactor 503 and the sample compactor will compress the remaining sample firmly into the sample cell as the cell progresses in motion toward positions IV and V. The applied pressure of compacting of the sample by the sample compactor 503 is born by compression roller 509 below the cell unit.

As the window-less cell full of sample reaches position IV the X-ray shutters 505 have also, in turn, moved away from beneath the X-ray analyzers FIGS. 4, 5, 6 507,508. FIG. 4 shows a typical X-ray spectroscope mounted within unit 508 and also contained within enclosure 521. The X-ray tube 1 with a target 2 selected according to the desired analysis. The target 2 is excited by the filament 3, primary X-rays 5 strike the sample in the cell 502 and secondary X-rays 4 emerge from the sample and cell. The secondary X-rays are collected by the spectroscopic detector 6 and are used to determine the assay. Primary X-rays 5 also leave the tube and penetrate the cell 502 to reach the density detector 506. This data is also used in determining the final assay and the packing factor.

Another typical X-ray spectroscope FIG. 5., may be used in conjunction with the first X-ray unit in 508. This second X-ray is mounted in unit 507 and also contained within enclosure 522. The second X-ray tube 11 with a target 12 selected according to the desired analysis. The target 12 is excited by filament 13, primary X-rays 15 emerge and strike the sample in cell 502. Secondary X-rays 14 merge from the sample in cell 502 and enter detector 16 and are used to determine the assay of the sample and may be used in conjunction with the data from the first X-ray unit.

FIG. 6 shows another typical X-ray spectroscope that may be used in place of either the first or second X-ray unit. This X-ray unit is a Radio-active X-ray spectroscope 21 and may be within 508 and also contained within 521. The Radioactive source 22 emits primary radiation 25 into the sample in the cell 502 and secondary radiation 24 merges from the sample and enters the detector 26. Primary radiation 25 also penetrates the sample in the cell and enters the density detector 506. Data from the assays are used to determine the elemental content of the sample.

The sample in the cell is then progressively analyzed firstly by one mode of X-ray analysis 507 and then by another second form of X-ray analysis 508 if required. The analyzed data is accumulated from the secondary radiation detector over the full length of the window-less sample cell and as the window-less cell passes through the analyzer beams data are integrated according each element of interest and density.

Data on density and cell packing factor are collected and accumulated by X-ray detector 506 and integrated with all the other density data accumulated from the X-ray analyzers 507,508.

Figure 1A:
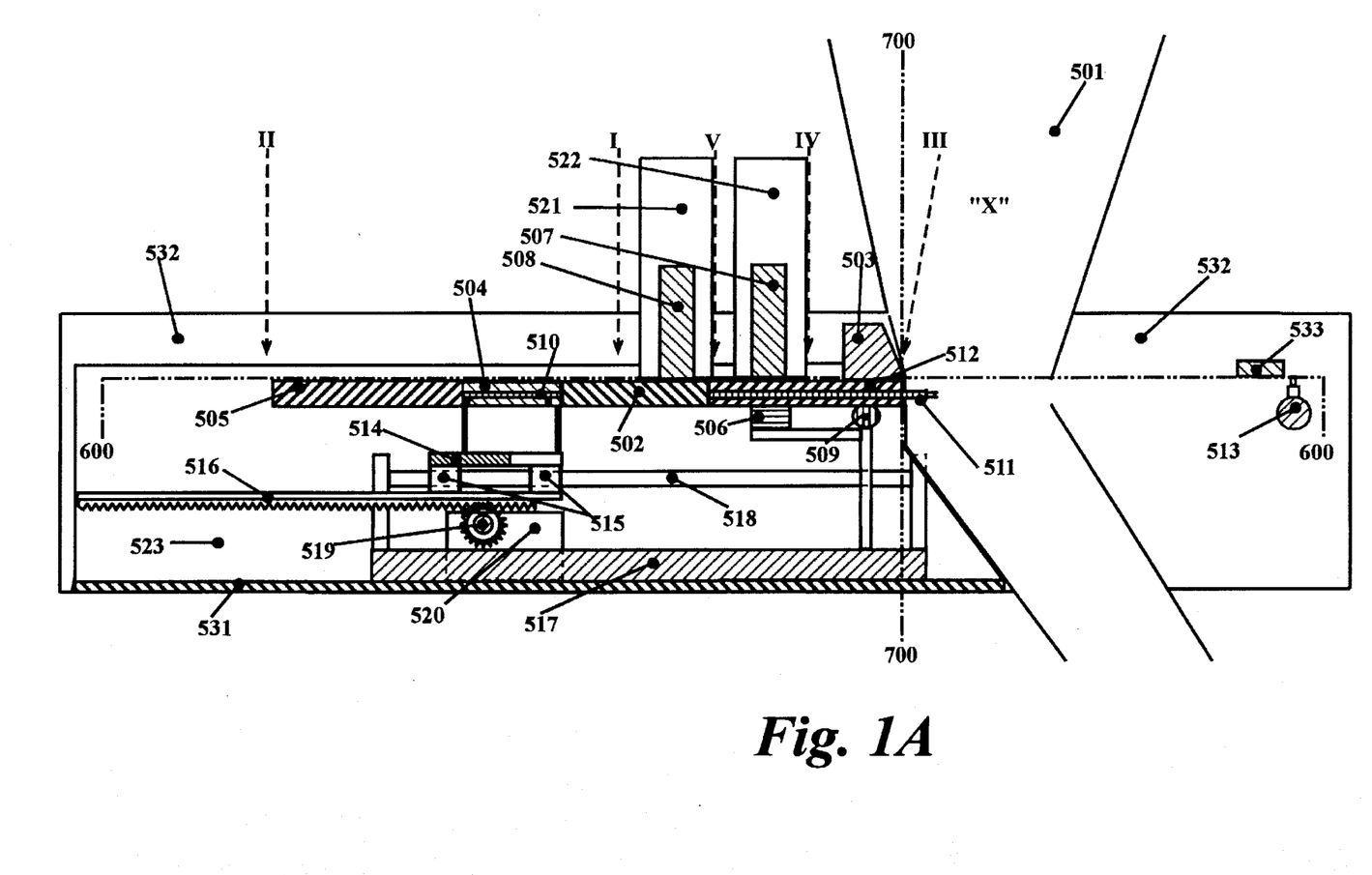
FIG. 1A, similarly, is a drawing that shows the relationship of the same units as in FIG. 1, at the side elevation at section 500—500 of FIG. 2. The difference is that the window-less sample cell 502 is now at position III and the window-less sample cell transportation unit is in the sample analyzing position under the second X-ray unit at position II or at the end of the forward movement, ready to now reverse motion and return to positions III & I.
Figure 2:
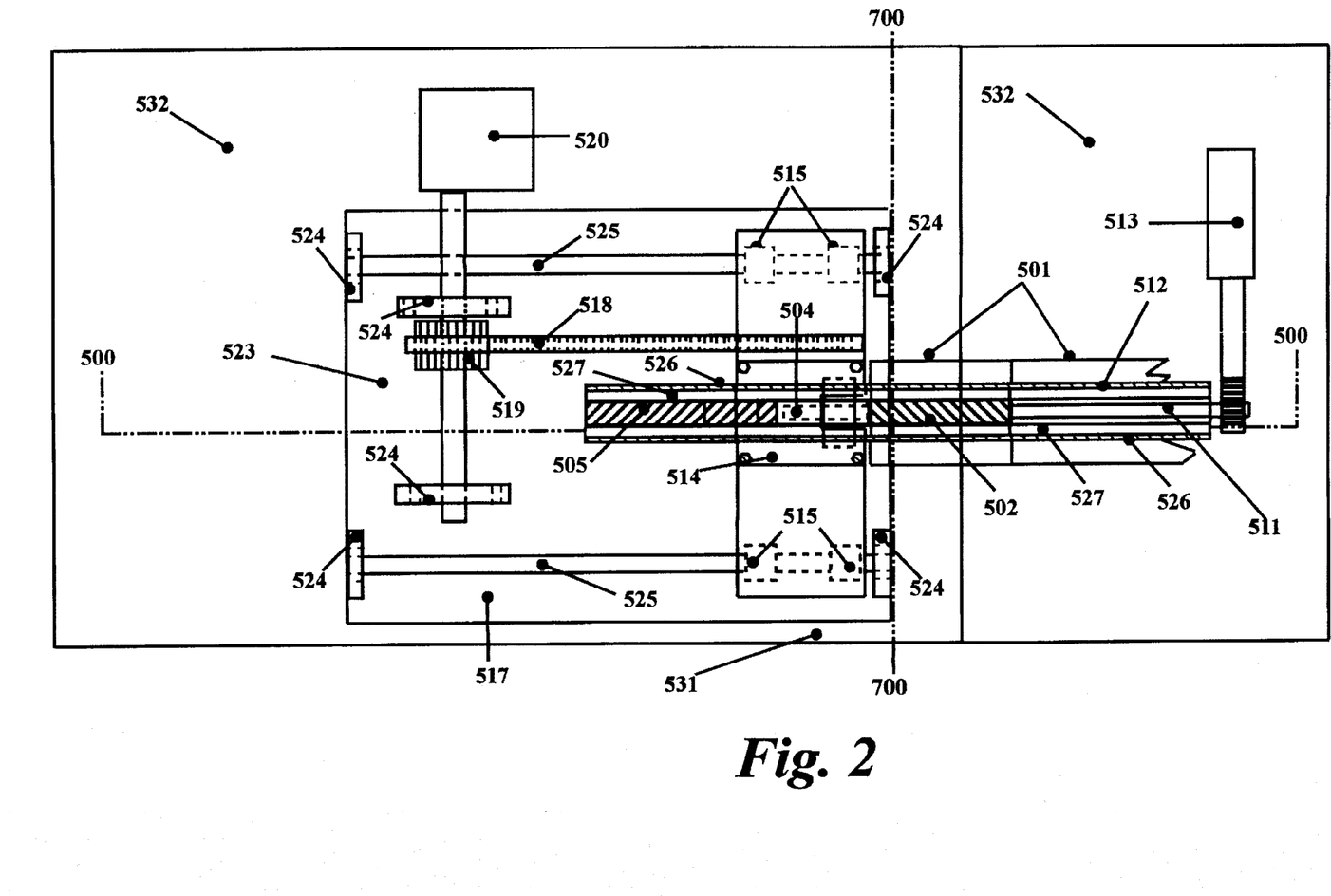
FIG. 2 shows a plan view of section 600—600 of FIG. 1, where the stepping motor drive is visible and the window-less analyzing sample cell is in the sample loading position III, or zero or start position. Also visible are the window-less sample cell transport platform at position I, the linear bearing rods, the cell support straps and the cell rotation actuator.
Figure 3:
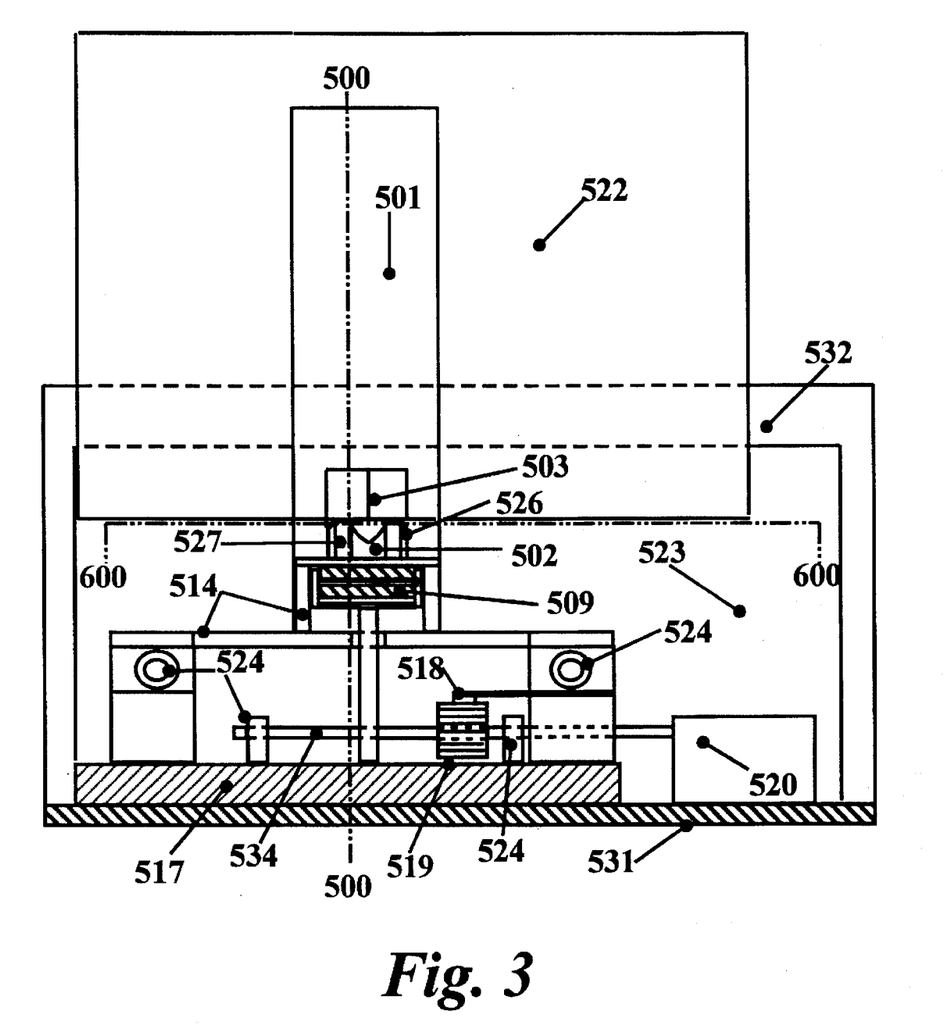
FIG. 3. Is a front view section 700—700 of FIG. 2 showing the same relationship of all the major units.

As the front of the cell 505 goes from linear position I and then reaches linear position II, the motor and gear drive direction is reversed, FIG. 1A. The analytical window-less sample cell then moves to return to the start, filling position III. FIGS. 1,1A, 2. Additional data is accumulated from the sample as the window-less cell passes once again through the path of the X-ray analyzers 508,507 and returns to the start position. On reaching the start position III the motor 520 and gear drive 519,518 stop and the sample rotation actuator 513 rotates the window-less sample cell 502, 180° on the window-less cell beatings 510,511 and discharges the sample which falls into the exit chute "x". The unit 512 is prevented from rotating by a stop part 533. Following the discharge of the previously analyzed sample, the window-less cell 502 is again rotated −180° to return to its former upright position ready for reception of the next portion of sample to be analyzed. Sensing of the carriage position is provided by standard position switch means.

For the purposes of obtaining maximum intensity from samples having low concentrations of the lighter elements, provision is provided for evacuating internal areas of the X-ray analyzers 521,522 and filling them with Helium. Similarly, areas 523 FIG. 1, FIG. 1A, FIG. 2 and FIG. 3 are also filled with Helium. The entire unit is supported on base 531 and covered by exterior covers 526,532.

The invention claimed is:

1. An apparatus for collecting, retaining, transporting, analyzing by X-ray spectroscopy means and the discharging of powder samples, comprising a mechanical system, having a window-less sample cell constructed with four walls, a closed side and one open side, the open side being uppermost to permit the acceptance and discharge of powder samples said window-less sample cell being mounted on a window-less sample cell transportation unit, said window-less sample cell transportation unit comprising of an associated window-less sample cell mounting platform supporting two linear bearing rods in turn supporting four linear sliding bearings mounted upon the two linear bearing rods, said window-less cell is filled with a sample of a product stream flowing through the sample inlet chute, said sample being a flowing portion of a main product or process stream, said window-less sample cell containing said sample is moved horizontally forward away from filling position by said window-less sample cell transportation unit by motor drive means and said window-less sample cell and said sample passes between a sample compactor unit and lower roller pressure support unit mounted integrally on said window-less cell mounting platform, excess said sample powder is removed from said window-less sample cell by said sample compactor and said sample in said window-less sample cell is compressed by said sample compactor and said compactor pressure is supported by said lower roller pressure unit, surface of said sample being compressed by said sample compactor and is smoothed into a continuous surface, said window-less sample cell and sample continue to move and, said window-less cell transportation unit continues to move and is attached to safety shutters of associated X-ray spectroscopy units having beams of X-ray radiation to excite the elements in the sample and emit secondary elemental radiation which is then absorbed by the associated X-ray detectors, and said X-ray safety shutters are now pushed away from said X-ray spectroscopic beams and said associated X-ray detectors permitting said sample in said window-less sample cell to be bombarded by said beams of X-rays of first X-ray spectroscopic systems and the said sample analyzed by means of said beams of X-rays, and the emanating elemental data are collected by said first X-ray system detectors and the resultant secondary radiation data being the elemental assay of said sample in said window-less sample cell and where said X-ray beams pass through said sample in said window-less cell and said X-ray radiation beam is detected by X-ray density detector situated below said sample and said window-less sample cell, X-ray density, packing factor data are accumulated together with the elemental data and transmitted to micro-processor means and, said window-less sample cell transportation unit continues to move said window-less sample cell and said sample into the second X-ray spectroscopic system beams of radiation and associated X-ray detectors and as in the first X-ray spectroscopic unit the ensuing secondary radiation data is collected by said second X-ray system detectors and the resultant data being the elemental assay of said sample in said window-less sample cell and said data from said second X-ray system is collected and manipulated by said microprocessor means, said window-less sample cell transportation unit now stops and reverses direction and said window-less sample cell and said sample are now transported in the reverse direction toward said filling position and said X-ray spectroscopic beams are continuously analyzing said sample until said X-ray safety shutters are closed by said window-less sample cell transportation unit and said window-less sample cell and said sample are now at the said filling position and, said X-ray beams and said X-ray detectors may analyze all said samples for many elements from Na to U and all data relating to elemental composition, particle size, density, compaction of sample are presented to said micro-processor means and, said first and said second X-ray tubes employ X-ray tube targets selected from a group which consists of W, Cr, Cu, Mo, Pt, Ag, Rh and said associated detectors are selected to accept all said X-ray primary and secondary beam energy levels emanating from said sample, said window-less sample cell transportation unit is now stationary said window-less sample cell is rotated 180° to discharge said sample from said window-less sample cell into said sample chute, said window-less sample cell is now empty of said sample and said window-less sample cell is now rotated in reverse 180° to bring said window-less sample cell into the original upright start filling position and, said window-less sample cell transportation unit repeats all said processing movements to analyze singly and repetitively all said samples presented to said window-less sample cell unit and, where said window-less sample cell transportation unit is manufactured to a size commensurate with analyzing variable quantities of said samples within a given period and where the dimension and composition of said window-less sample cell is variable and, where motions of said window-less sample cell transportation unit and said window-less sample cell unit maybe varied for speed of operation and duration time of analysis and, said window-less sample cell transportation unit and said window-less sample cell, are manufactured in a size commensurate where said samples may be inserted manually and sequentially into said window-less sample unit as in a manual laboratory mode, and said samples analyzed in said window-less cell in an automated mode in the said window-less sample cell transportation unit and, where said window-less sample cell transportation unit and said window-less sample cell and said window-less sample cell transportation unit motions, operations and sequential movement of the said window-less sample cell system are controlled and programmed, where data from said X-ray spectroscopic elemental detectors and said associated density are collected, evaluated, processed for all standard and test samples and, said window-less sample cell transportation unit is equipped with apparatus for inserting an atmosphere of helium gas means into areas of said X-ray spectroscopic analytical beams and said X-ray detector units and said window-less sample cells to analyze elements ranging from Na to U within said samples and said window-less sample cells and, where said window-less sample cell transportation unit of claims listed above, said motions of said sample and said window-less sample cells may be a rotating function.

2. The apparatus of claim 1, where the elemental analysis of said samples is achieved using radioactive isotope X-ray spectroscopic source means and with associated elemental X-ray detector means.

3. The apparatus of claim 2, where a plurality of said different X-ray spectroscopic excitation sources and associated elemental detector means and associated density and intensity detector means, are combined in places designated for analysis.

* * * * *